United States Patent
Amendt et al.

(10) Patent No.: US 10,245,168 B2
(45) Date of Patent: Apr. 2, 2019

(54) ARRANGEMENT FOR IMPLANTING STENT ELEMENTS IN OR AROUND A HOLLOW ORGAN

(71) Applicant: MEDIGROUP GMBH, Pforzheim (DE)

(72) Inventors: Klaus Amendt, Mannheim (DE); Johannes Jung, Pforzheim (DE); Heinz Kölble, Ettenheim (DE)

(73) Assignee: MEDIGROUP GMBH, Pforzheim (DE)

( * ) Notice: Subject to any disclaimer, the term of this patent is extended or adjusted under 35 U.S.C. 154(b) by 42 days.

(21) Appl. No.: 14/357,348

(22) PCT Filed: Nov. 12, 2012

(86) PCT No.: PCT/EP2012/004696
§ 371 (c)(1),
(2) Date: May 9, 2014

(87) PCT Pub. No.: WO2013/068127
PCT Pub. Date: May 16, 2013

(65) Prior Publication Data
US 2014/0288629 A1    Sep. 25, 2014

(30) Foreign Application Priority Data

Nov. 11, 2011 (DE) .................. 10 2011 118 414
Nov. 11, 2011 (DE) .................. 20 2011 107 781 U
Nov. 9, 2012 (WO) ................ PCT/EP2012/004666

(51) Int. Cl.
*A61F 2/962*    (2013.01)
*A61F 2/82*    (2013.01)

(52) U.S. Cl.
CPC ........ *A61F 2/962* (2013.01); *A61F 2002/828* (2013.01)

(58) Field of Classification Search
CPC .................. A61F 2/89; A61F 2002/828; A61F 2002/826; A61B 2017/00314
See application file for complete search history.

(56) References Cited

U.S. PATENT DOCUMENTS 5,833,694 A * 11/1998 Poncet ...................... A61F 2/95
                                                      623/1.11
7,137,993 B2 * 11/2006 Acosta ................... A61F 2/915
                                                      623/1.11

(Continued)

FOREIGN PATENT DOCUMENTS

DE    1 974 688 U    12/1967
DE    600 30 705 T2    5/2007

(Continued)

OTHER PUBLICATIONS

European Patent Office, First Office Action dated Oct. 22, 2015.

*Primary Examiner* — Alexander J Orkin
(74) *Attorney, Agent, or Firm* — Hudak, Shunk & Farine Co. LPA

(57) ABSTRACT

Arrangement for implanting stent elements in or around a hollow organ, having a plurality of stent elements, more particularly self-expanding stent elements, wherein the stent elements are arranged on an axial line (L) and wherein lateral surfaces of the respective stent elements are defined by material-free regions and material webs.

8 Claims, 2 Drawing Sheets

(56) References Cited

U.S. PATENT DOCUMENTS

| | | | |
|---|---|---|---|
| 8,348,994 B2* | 1/2013 | Leopold | A61F 2/885 623/1.16 |
| 9,254,212 B2* | 2/2016 | Papp | A61F 2/958 |
| 2002/0120323 A1* | 8/2002 | Thompson | A61F 2/91 623/1.11 |
| 2004/0059407 A1* | 3/2004 | Escamilla | A61B 17/12022 623/1.12 |
| 2004/0215331 A1* | 10/2004 | Chew et al. | 623/1.21 |
| 2005/0149168 A1* | 7/2005 | Gregorich | 623/1.15 |
| 2006/0058865 A1* | 3/2006 | Case | A61F 2/95 623/1.11 |
| 2006/0069424 A1* | 3/2006 | Acosta | A61F 2/91 623/1.12 |
| 2006/0184225 A1* | 8/2006 | Pryor | A61F 2/91 623/1.11 |
| 2006/0184227 A1* | 8/2006 | Rust | A61F 2/07 623/1.13 |
| 2007/0043419 A1* | 2/2007 | Nikolchev | A61F 2/90 623/1.11 |
| 2007/0156223 A1* | 7/2007 | Vaughan | A61F 2/95 623/1.11 |
| 2007/0219612 A1* | 9/2007 | Andreas et al. | 623/1.11 |
| 2008/0154351 A1* | 6/2008 | Leewood | A61F 2/86 623/1.2 |
| 2008/0221657 A1* | 9/2008 | Laroya | A61F 2/885 623/1.12 |
| 2008/0234795 A1 | 9/2008 | Snow et al. | |
| 2009/0171427 A1* | 7/2009 | Melsheimer | A61F 2/95 623/1.11 |
| 2010/0152835 A1* | 6/2010 | Orr | 623/1.15 |
| 2012/0035705 A1* | 2/2012 | Giasolli | A61F 2/86 623/1.12 |

FOREIGN PATENT DOCUMENTS

| | | |
|---|---|---|
| EP | 1894545 A1 | 3/2008 |
| WO | 2006026371 A1 | 3/2006 |

* cited by examiner

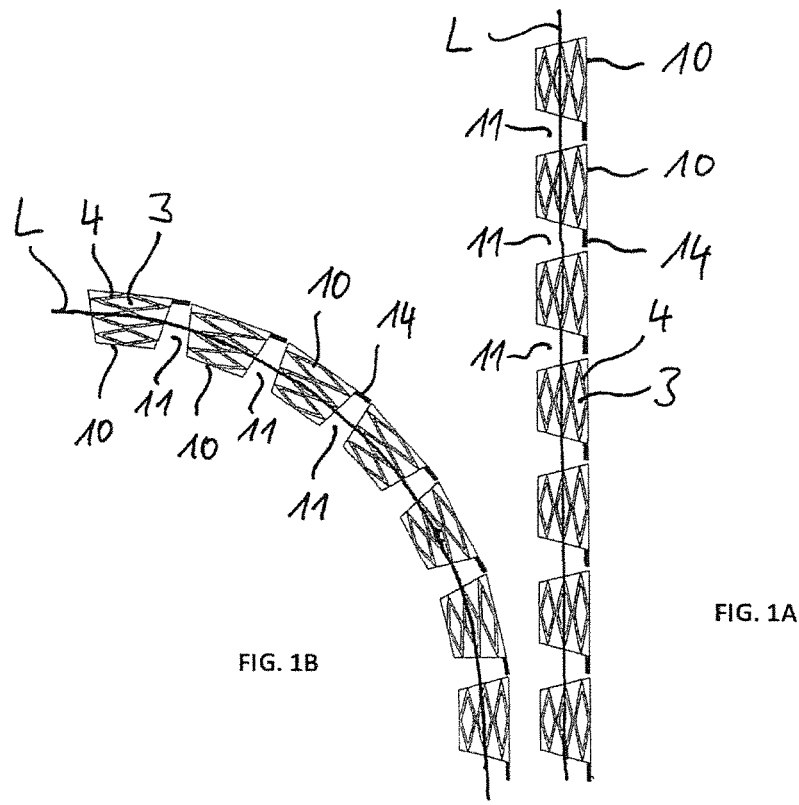
FIG. 1A
FIG. 1B
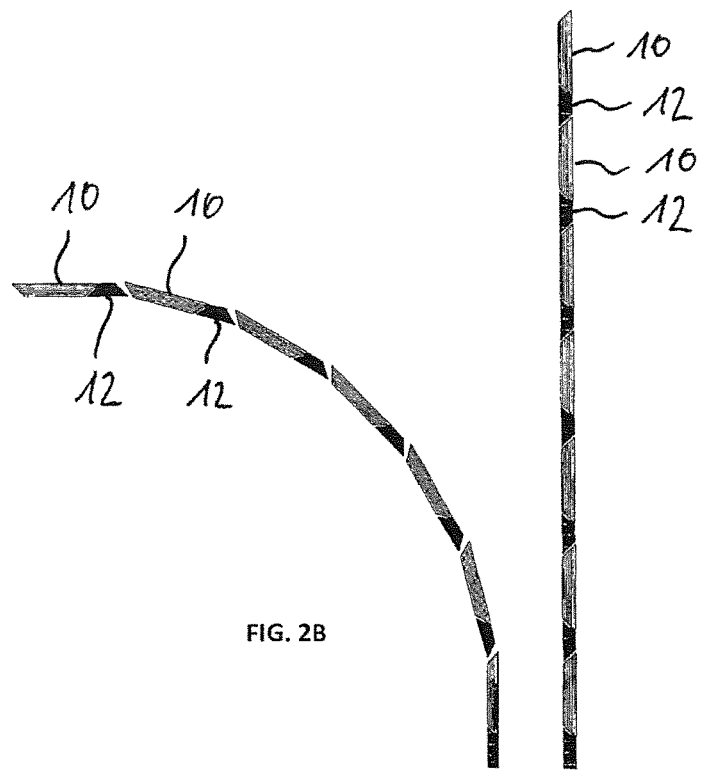
FIG. 2A
FIG. 2B

ARRANGEMENT FOR IMPLANTING STENT ELEMENTS IN OR AROUND A HOLLOW ORGAN

FIELD OF THE INVENTION

The invention concerns an arrangement for installing at least one stent element in a hollow organ, comprising a shaft with a proximal end and a distal end having an atraumatic tip, and at least one stent element arranged on an axial line inside the shaft, wherein the shaft prevents an expanding of the stent element, and a plurality of independent stent elements are arranged alongside each other on the axial line.

BACKGROUND OF THE INVENTION

Stents are used as prostheses for expanding and holding open in tubular hollow organs such as blood vessels. Such stents generally have a latticelike or spiral-shaped structure of material webs. Between the material webs, regions free of material are formed, which make it possible for this structure to grow into the tissue at its implantation site. Such stents are described, for example, in DE-A 197 46 88.

In bendable vascular regions such as in the knee, the prostheses of the prior art have the problem that substantial pushing, pulling and twisting movements occur in the region of the bending by the stent. Furthermore, additional frictional forces also act there on the intima of the blood vessels. Moreover, the aforementioned resulting pushing, pulling and twisting movements weaken the material webs, so that breakage and individual detachments of stent fragments can occur. This, in turn, can lead to injuries to the vascular wall, a restenosis, for example by scar formation on the vascular wall, or even the triggering of an aneurysm. Embolisms can also be triggered by this.

In publication DE 600 30 705 T2 a catheter is described for implanting of a stent, having a sheath, while a multiple-piece stent can be present in the sheath. The multiple-piece stent consists of neighboring stent pieces, which are joined together by connection elements. When the stent is inserted into an artery, the connection element is physically separated from an adjacent stent piece by an expansion of the stent piece. However, an exact laying or placing of the individual stent piece is nearly impossible in this case, since such a physical separation of the stent pieces is not always uniform. What is more, there is the disadvantage that traces of the connection elements remain on the stent pieces in place, which in turn can contribute to injury of the vascular wall.

SUMMARY OF THE INVENTION

One problem of the invention is to provide an arrangement for the inserting of at least one stent element into a hollow organ so that, among other things, the described disadvantages are avoided when implanted in bendable vessels. Furthermore, an arrangement is to be provided that allows the doctor to install stents in different parts of the body with the aid of a single implantation kit or catheter.

The problem is solved by the arrangement for implanting of stent elements in a hollow organ comprising at least one shaft with a proximal end and a distal end having an atraumatic tip, and wherein the at least one stent element is arranged on an axial line (L) inside the shaft and the shaft prevents an expanding of the stent element, wherein a plurality of independent stent elements are spaced apart by one or more spacers and arranged alongside each other on the axial line (L). Advantageous modifications and preferred embodiments are given in the subclaims.

The arrangement according to the invention is intended for installing or implanting at least one stent element in a hollow organ, especially a blood vessel. Instead of a single, more or less flexible, oblong tubular stent, it is proposed for form the arrangement according to the invention from a plurality of independent stent elements, especially short stent elements, which are arranged on an axial line, while each time a spacing is formed between neighboring elements, such that the elements can be installed or implanted without problem, individually and independently in time from each other. Thanks to the implanting of several individual stents, not connected to each other, and which are therefore freely movable independently of each other, a frictional strain on the inside of the vessels is prevented. Furthermore, it is possible to apply stents at totally different places in the body with the aid of a single catheter/kit. This not only eases the stress on the patient, but also leads to a substantial cost savings.

The stent elements are freely movable in the sense of the invention because they are not connected to each other after the implantation, i.e., they are only freely movable in relation to each other, while the intended connection of the stent to the tissue of the vascular wall is naturally created. This advantageously reduces the friction against the vascular wall during the bending of a vessel. The inside of the vascular inner wall is usually wave-shaped due to the compression during the bending. In the arrangement according to the invention, the advantageous possibility exists of these compressed vessel regions penetrating into the spaces between the stent elements, which additional irritation being caused here. Likewise, the mutually independent stent elements prevent a direct transmittal of force, which prevents stresses in the lateral surfaces of the stent elements defined by the material-free regions and material webs.

The axial line on which the stent elements are arranged is introduced within the shaft into the vessel during the implantation. The lateral surfaces of the tubular elements enclose the axial line at a radial spacing. Preferably, the stent elements are self-expanding or self-expandable and have a smaller radial dimension prior to the implantation and expand during or after the implantation to a larger radial dimension. Advantageously, the axial line is elastic, especially bending elastic.

The stent elements according to the invention are formed in particular as a single piece, preferably made of metal, while especially preferably the stent elements are cut out of a single metal tube. The cutting can be done in particular with lasers or other suitable high-precision controlled cutting implements. Cutting in the sense of the invention means any suitable method for creating the structures according to the invention. The cutting pattern is freely optional. Preferably, however, elastic and especially bending elastic cutting patterns are preferred. At any rate, a simple diamond-shaped cutting pattern is preferred.

In the arrangement according to the invention, the individual pieces of the stent elements preferably prior to their implanting on or in the arrangement are joined together firmly and optionally by means of spacers, and do not adhere together only at one or a few places. The stent elements can consist of any desired material, as long as it is suitable for use in the human body and as long as it has the needed properties for a stent, such as elasticity and adequate supporting function. Typical materials are, in particular, refined steel or a nickel and titanium alloy, preferably a Nitinol or other shape-memory alloy. The surface is optionally electroplated and/or electropolished or otherwise refined to ensure a sufficiently smooth and tolerated surface. Furthermore, the stent elements are preferably radiologically opaque or at least have radiologically opaque markings, which allow the treating physician to position the stent elements as accurately as possible during their placement, since this can make visible the position of each individual stent element. This also enables a checking of the position of the stent elements afterwards in the following medical examinations.

The lateral surfaces of the stent elements are advisedly cylindrical. Optionally, the elements have a bevel at only one or at both axial ends. It is generally provided according to one preferred embodiment that a height of the lateral surface of at least one stent element varies across a circumference of the lateral surface. In this way, that region of the lateral surface which has a curtailed height can be arranged in the region of the inner curvature of the bent vessel, which enlarges the intermediate spaces into which the compressed vascular wall can penetrate during the bending. Preferably for this, a maximum of the height of the lateral surface is arranged opposite a minimum of the height of the lateral surface on the circumference of the stent elements, which produces a longitudinal cross section of diamond shape.

As compared to the prostheses of the prior art, the stent elements of the invented arrangement are preferably shortened so that, according to one preferred embodiment, a ratio between a maximum length of the lateral surface and a diameter of at least one stent element is at least 1.0, especially at least 1.5 or 1.8 or 2. Especially preferred are ratios of at least 2.3. Typical upper limits for the ratio are a maximum of 8 or 6, especially a maximum of 5, with special preference to a maximum of 4 or 3.5.

According to another preferred embodiment of the invention, spacers are arranged between the stent elements prior to the implantation. This simplifies the installing or placement of the stent elements, especially since the individual elements are to be arranged with a spacing from each other. For this, the spacers preferably have a shape complementary to the stent elements, at least prior to implantation, it being noted that the shape of the spacers should preferably be coordinated with the shape of the stent elements so that the spacers fill up the space between two neighboring elements.

In this way, the arrangement of the invention makes it easier to handle the placement of the stent elements, which is especially advantageous, since each stent element needs to be placed in its axial position not only by transport along the vessel length, but also positioned by an appropriate twisting so that the inner side of the bending of the vascular inner wall is coordinated with the region with shortened length of the lateral surface, and the region with greater length is coordinated with the outer side of the bending of the vessel. Such a stent element has a conical or trapezoidal, optionally also an orthogonally trapezoidal cross section. However, the prostheses according to the invention can also comprise cylindrical stent elements or even consist exclusively of such types. The spacers with their stabilizing action enable a movement of the stent being put in place as if only one elongated stent element were being put in place. In the case of self-expandable stent elements, the complementary shape of the spacers corresponds to the shape of the stent elements with smaller radial dimension, which the stent elements have until being implanted. After the expansion to the larger radial dimension, the spacers are preferably no longer complementary in shape, since the spacers keep their original shape and do not expand.

Especially preferably, the shaft with optionally interior axial line with again optionally mounted stent elements and/or spacers can be guided through the inside or the inner volume of the stent elements after the implantation. In this way, the spacers can be removed once more after the installing of the stent elements, possibly even through already positioned and expanded stent elements. Thus, additional stent elements could also be installed before and/or after the already implanted stent element. It is also possible in the sense of the invention to place an additional stent element inside an already expanded and placed stent element with the arrangement of the invention, which will double or intensify the outwardly acting radial force. The spacers can optionally be joined together, e.g., on a thread, a wire, or a sleeve, being configured as an axial line. The spacers usually consist of the same material as the stent elements. However, they can also consist of any other compatible material, such as plastic. They can be radiologically opaque or not. The arrangement of the stent elements makes it possible to lay down the stent elements so that they are positioned optimally each time, even under extremely twisted strains or lesions.

According to another preferred embodiment of the invention, the stent elements are detachably connected by means of spacers as a coupling element or connection anchor, which further improves the stability when placing the stent elements. Especially preferred, the particular connection can be separated by an expanding of the stent element during the implanting. For this, the connection is form-fitting especially in the axial direction, but not in at least one radial direction, so that the expansion of the stent element during the installation automatically results in a separating of the connection.

The invention also specifies a method for installing at least one stent element in or around a hollow organ, by placement of a plurality of stent elements, especially self-expandable stent elements, wherein lateral surfaces of the particular stent elements are defined by material-free regions and material webs, and the stent elements are arranged on an axial line so that each time a space is formed between neighboring stent elements, and the stent elements are freely movable after the implanting.

Preferably, spacers are arranged between the stent elements prior to the implanting. Furthermore, the stent elements are detachably connected to the particular adjoining spacers prior to the implanting. Furthermore, the stent elements are separated from the spacers by expanding during the implanting. Moreover, the spacers after the implanting are preferably guided through the stent elements in order to advantageously remove the spacers.

BRIEF DESCRIPTION OF THE DRAWINGS

The invention is described more closely below by means of sample embodiments in drawings. The explanations are merely an example and do not limit the general notion of the invention.

There are shown:

FIGS. 1A and 1B, expanded stent elements after the implantation by means of the arrangement according to the invention in a schematic representation;

FIGS. 2A and 2B, nonexpanded stent elements prior to the implantation by means of the arrangement according to the invention in a schematic representation;

DETAILED DESCRIPTION OF THE INVENTION

Figure 3:
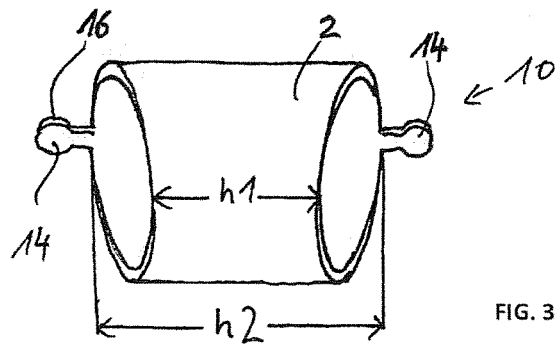
FIG. 3, a stent element in a perspective representation.

In FIGS. 1A and 1B, each time a plurality of tubular stent elements 10 are shown, which are arranged on an axial line L, the line L being straight in FIG. 1A and curved in FIG. 1B, in a side view after the implanting with the aid of the arrangement according to the invention. This makes it clear that each time a spacing 11 is formed between neighboring stent elements 10, by which the stent elements are freely movable after the implanting.

The benefit of the arrangement according to the invention is that the stent elements 10 after placement in the vessel or hollow organ are not connected together and an undulating compressed vascular inner wall during bending can escape into the free spaces 11 between the stent elements 10. This likewise prevents an irritation of the tissue, such as an excessive stress load caused by the structure of the stent elements 10, formed from material-free regions 3 and material webs 4. One can see connection anchors 14 on the stent elements 10, which are not connected to the respective neighboring stent. For reasons of clarity, only some of the units which are repeated for each stent are given a reference number.

The stent elements 10 shown in FIGS. 1A and 1B are drawn in the condition after the implanting, especially in an expanded state, since the stent elements 10 are preferably self-expandable. The state prior to implanting, shown in FIGS. 2A and 2B, is the state according to the invention in which the stent elements 10 have up to the individual installation. The stent 10 in place thus constitutes the state after the implanting in the sense of the invention. Thus, as regard all stent elements which are comprised in an embodiment of the invented arrangement, some of the stent elements 10 can also be in the state prior to implanting, while others have already passed to the state after the implanting.

The stent elements shown in FIGS. 2A and 2B show all stent elements 10 prior to implanting in a nonexpanded state, each time connected by spacers 12, which have a shape complementary to the stent elements 10, and thus make up a continuous cylinder shape with them. The stent elements 10 have a trapezoidal projection in side view, which is produced by beveled axial ends of the tubular stent element 10 each time, as shall be further discussed below in connection with the later discussed figures.

FIG. 3 shows an individual stent element 10 in a perspective representation, the structure of the lateral surface 2 being shown schematically smooth here. Essentially, the relatively short stent elements can have the shape of a hollow cylinder of constant height. Preferably, the lateral surface 2 has a variable height along the circumference, while in the drawing a minimum height h1 is arranged opposite a maximum h2 on the circumference. If the stent element 10 with the minimum height h1 is turned toward the undulating compressed vascular inner wall during a bending, larger spaces 11 (see FIG. 1B) are advantageously available between the stent elements 10. For the connection to the spacers 12 shown in FIGS. 2A and 2B, the stent element 10 has a connection anchor 14, for example, at either end. Again, preferably, the stent element 10 is radiologically opaque or provided with a radiologically opaque marker 16, which is especially preferably arranged on the connection anchor 14.

Figure 4:
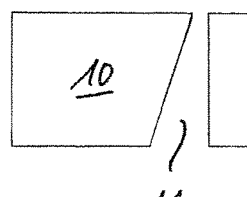
FIGS. 4 and 5, several mutually independent stent elements after the implantation by means of the arrangement according to the invention in a schematic representation.
Figure 5:
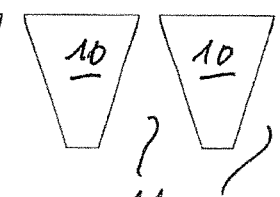

FIGS. 4 and 5 illustrate further examples of possible shapes of the stent elements 10, retaining the fundamental tubular shape. The configuration of the axial ends of the stent elements or the height of the lateral surface can be seen in the side view, as well as the corresponding effect on the spacings 11. In the example of FIG. 4, only one axial end of the stent elements 10 is slanting, which reduces the expense for the manufacture.

FIG. 5 shows stent elements 10 that have a distinctly smaller height of the lateral surface in the axial direction, this height in addition varying across the circumference, so that the minimum height is substantially shorter than the maximum. In this way, the stent elements 10 get a wedge shape with an almost pointed inlet.

Figure 6:
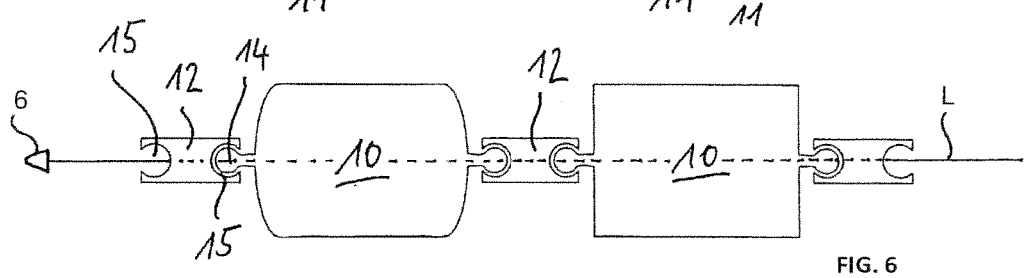
FIGS. 6 and 7, several stent elements as well as an axial line with spacers after the implantation by means of the arrangement according to the invention in a schematic representation.
Figure 7:
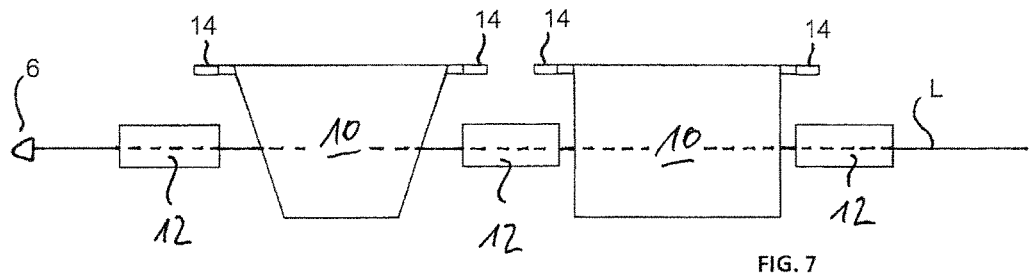

FIGS. 6 and 7 shall now explain more closely the connection of the stent elements 10 to the spacers 12 and especially its breaking. The spacers 12, which are arranged on an axial line L, have undercuts 15, in which the connection anchors 14 of the stent elements 10, which are likewise arranged on the axial line L, produce a form-fitting connection in the axial direction. The connection is broken by a relative radial movement of stent 10 and spacer 12, for example, by the expansion of the stent element 10 during the implanting. Optionally, in one advantageous embodiment of the arrangement according to the invention, the axial line L has an atraumatic tip 6 at the distal end.

Figure 8:
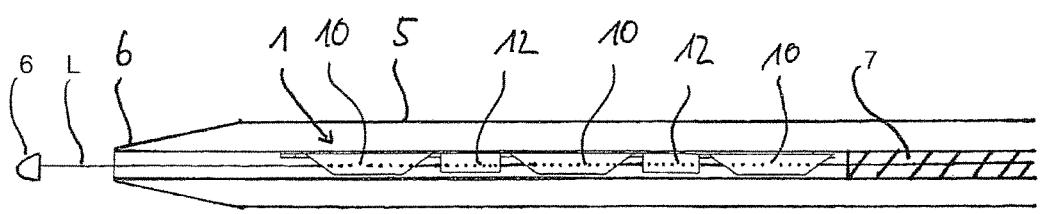
FIG. 8, an arrangement according to the invention for installing at least one stent element in a hollow organ in a schematic representation.

FIG. 8 shows an arrangement according to the invention for installing at least one stent element in a hollow organ, the arrangement comprising at least one shaft 5 with a proximal end and a distal end optionally having an atraumatic tip 6, and wherein several mutually independent stent elements 10 are arranged at a spacing next to each other on an axial line L inside the shaft 5, while the stent elements 10 each time are detachably connected to spacers 12. The shaft 5 prevents an expanding of the stent elements 10 and because the axial line is arranged inside the shaft 5 capable of displacement in the axial direction and rotation, it allows an exact positioning of the individual stent elements 10, which only expand after the withdrawal of the shaft or a distal axial displacement of the axial line L and thereby interrupt their connection to the spacers 12. The spacers 12 do not expand and advantageously they can be pulled back in the catheter shaft 5 through the expanded stent elements 10 after the implanting has been done, as is also clearly recognizable in FIG. 7. Optionally, in one advantageous embodiment of the arrangement of the invention, the axial line L has an atraumatic tip 6 at the distal end. In one preferred embodiment of the arrangement of the invention, a filler material is arranged inside the shaft 5 behind the axial line L mounted with the stent elements 10, to prevent a buckling of the shaft 5.

LIST OF REFERENCE NUMBERS

2 lateral surface
3 material-free region
4 material web
5 shaft
6 atraumatic tip
7 filler material
10 stent element
11 spacing
12 spacer
14 connecting anchor 15 undercuts
16 radiologically opaque marker
L axial line
h1 maximum height
h2 minimum height

What is claimed is:

1. An arrangement for installing at least one stent element in a hollow organ, comprising:
at least one shaft with a proximal end and a distal end having an atraumatic tip, a plurality of independent, single piece stent elements, said stent elements are arranged on an axial wire (L) inside the shaft and the shaft prevents an expanding of the stent elements, wherein the plurality of independent stent elements are not connected to each other and are spaced apart by one or more spacers that are arranged lengthwise of each other along the axial wire wherein the spacers have a shape complementary to adjacent stent elements, wherein the spacers are not detachably connected to said axial wire and do not expand so that they can be pulled back into the shaft through expanded stent elements wherein the stent elements have an anchor at a proximal end and at a distal end of the stent element, wherein the spacers have an opening therein that provide a form-fitting connection with at least one anchor whereby the stent elements are detachably connected to the spacers, wherein the form-fitting connection is detached by relative radial movement of the stent and the spacer as by expanding the stent element, wherein lateral surfaces of said stents enclose said axial wire at a radial spacing therefrom and wherein a height of said lateral surface of at least one stent element varies across a circumference of said lateral surface and the anchors are arranged along a maximum height of said lateral surface.

2. The arrangement according to claim 1, wherein the spacers have a shape complementary to the stent elements.

3. The arrangement according to claim 1, wherein a filler material is arranged inside the shaft and behind the axial wire occupied by the stent elements.

4. The arrangement according to claim 1, wherein the respective stent elements are defined by said lateral surfaces with material-free regions and material webs.

5. The arrangement according to claim 4, wherein the maximum of the height (h1) of the lateral surface is arranged opposite a minimum (h2) of the height of the lateral surface on the circumference.

6. The arrangement according to claim 4, wherein at least one stent element has a ratio between its maximum height of the lateral surface and its diameter between 0.5 and 6.

7. The arrangement according to claim 1, wherein the maximum of the height (h1) of the lateral surface is arranged opposite a minimum (h2) of the height of the lateral surface on the circumference.

8. The arrangement according to claim 5, wherein at least one stent element has a ratio between its maximum height of the lateral surface and its diameter between 0.5 and 6.

* * * * *